(12) United States Patent
Shibata et al.

(10) Patent No.: US 8,608,917 B2
(45) Date of Patent: Dec. 17, 2013

(54) REFERENCE ELECTRODE

(75) Inventors: Manabu Shibata, Kyoto (JP); Yasukazu Iwamoto, Kyoto (JP)

(73) Assignee: HORIBA, Ltd., Kyoto-shi (JP)

( * ) Notice: Subject to any disclaimer, the term of this patent is extended or adjusted under 35 U.S.C. 154(b) by 0 days.

(21) Appl. No.: 13/819,320

(22) PCT Filed: Aug. 25, 2011

(86) PCT No.: PCT/JP2011/069142
§ 371 (c)(1),
(2), (4) Date: Feb. 26, 2013

(87) PCT Pub. No.: WO2012/026514
PCT Pub. Date: Mar. 1, 2012

(65) Prior Publication Data
US 2013/0153417 A1 Jun. 20, 2013

(30) Foreign Application Priority Data

Aug. 27, 2010 (JP) ................................. 2010-191535
Aug. 27, 2010 (JP) ................................. 2010-191537

(51) Int. Cl.
C25B 11/04 (2006.01)

(52) U.S. Cl.
USPC ............. 204/290.03; 204/290.05; 204/290.06

(58) Field of Classification Search
USPC ........................................ 204/290.01–290.15
See application file for complete search history.

(56) References Cited

U.S. PATENT DOCUMENTS 7,628,901 B2 * 12/2009 Kakiuchi et al. .............. 204/435
2008/0000771 A1 * 1/2008 Kakiuchi et al. .............. 204/435
2009/0283404 A1 11/2009 Kakiuchi et al.

FOREIGN PATENT DOCUMENTS

| EP | 2075574 A1 * | 7/2009 |
| JP | 2007064971 A | 3/2007 |
| JP | 2009156836 A | 7/2009 |
| WO | 2008032790 A1 | 3/2008 |

OTHER PUBLICATIONS

T. Kakiuchi and T. Yoshimatsu, "A new salt bridge based on hydrophobic room-temperature molten salt" Chemical Society of Japapn Bulletin, vol. 79, No. 7, 2006, p. 1017-1024.*
Kakiuchi, T. et al., "New Class of Ag/AgCl Electrodes Based on Hydrophobic Ionic Liquid Saturated with AgCl", Analytical Chemistry, vol. 79, No. 18, pp. 7187-7191, Sep. 15, 2007, 6 pages.
Kakiuchi, T., "Shin Byori no Enkyo o Tsukuru", Chemistry & Chemical Industry, vol. 61, No. 11, pp. 1053-1055, Nov. 1, 2008, 16 pages.
ISA Japanese Patent Office, International Search Report of PCT/JP2011/069142, Oct. 4, 2011, WIPO, 2 pages.

* cited by examiner

*Primary Examiner* — J. Christopher Ball
(74) *Attorney, Agent, or Firm* — Alleman Hall McCoy Russell & Tuttle LLP

(57) ABSTRACT

A reference electrode for improving a product life cycle without using a gelled hydrophobic ionic liquid having a prescribed hardness or viscosity and without having a large thickness so as to be difficult to manufacture is provided. The reference electrode is provided with a housing for accommodating an internal electrode, a filler for electrically connecting the internal electrode, and a sample liquid. The filler is formed having a layer between the internal electrode and an opening formed in the housing for contacting the sample liquid and the filler. The filler includes a first layer including a water soluble electrolytic solution formed to be in contact with the internal electrode a second layer including a hydrophobic ionic liquid formed to be in contact with the first layer; and a third layer including a gelled hydrophobic ionic liquid formed in the opening so as to be in contact with the second layer.

9 Claims, 9 Drawing Sheets

REFERENCE ELECTRODE

TECHNICAL FIELD

The present invention relates to a reference electrode used as a reference of calculation of an electrode potential or an electrochemical measurement.

BACKGROUND ART

An internal electrode used for indicating a fixed reference potential in pH measurement etc., is configured in such a manner that the internal electrode including, for example, silver/silver chloride and the like is immersed in an internal liquid including a high-concentration KCl solution so that this internal liquid may contact a sample liquid via a liquid junction including a porous member such as ceramic, glass and the like.

Accordingly, if a high-concentration KCl solution is used as an internal liquid of a reference electrode, $K^+$ and $Cl^-$ flow into a sample liquid side and KCl flows into the sample liquid via the liquid junction, and therefore the KCl concentration of the internal liquid will be reduced. In order to prevent fluctuations of the reference potential due to this reduction of the KCl concentration, it is necessary to frequently fill up and exchange the internal liquid. In addition, in consideration of volatility as a liquid of the internal liquid, there is also a limitation that it is necessary to have a large volume in the support tube which accommodates the internal liquid.

For example, in order to prevent fluctuations of a potential difference between the liquids, clogging of the liquid junction, and reduction of the KCl solution due to an outflow thereof into the sample liquid, the liquid junction includes a gelled hydrophobic ionic liquid configured to be used as a salt bridge while using the KCl solution as the internal liquid, and regarding such a reference electrode, the present applicant has filed prior patent applications (see Patent Literatures 1 and 2).

However, in these reference electrodes, ions of an ionic liquid slightly flow out into a sample liquid from a gelled hydrophobic ionic liquid contacting the sample liquid. Therefore, the ionic liquid in the gel may become a prescribed quantity or lower, and it may possibly be difficult to increase a life cycle of a product.

In order to address such a problem, although it may be considered that a thickness of the gel of the hydrophobic ionic liquid is made large so as to contain a lot of ionic liquid, it is very difficult in manufacturing technique with a great increase in cost to make the thickness and size of the gel large while maintaining, for example, the hardness in a degree capable of keeping a shape only by the gel of the hydrophobic ionic liquid.

CITATION LIST

Patent Literature

Patent Literature 1: JP2007-64971A
Patent Literature 2: International Publication WO 2008/032790

SUMMARY OF INVENTION

Technical Problem

The present invention has been made in consideration of the problems mentioned above, and an object thereof is to provide a reference electrode capable of improving a product life cycle without the necessity of using a gelled hydrophobic ionic liquid having a prescribed or more hardness or viscosity and having a large thickness and the like so as to be difficult to manufacture the same.

Solution to Problem

Accordingly, a reference electrode comprising an internal electrode and a housing that houses a filler for electrically connecting the internal electrode and a sample liquid, wherein the filler forms layers between the internal electrode and an opening formed in the housing for contacting the sample liquid and the filler, wherein the filler comprises: a first layer which includes a water soluble electrolytic solution formed to be in contact with the internal electrode; a second layer which includes a hydrophobic ionic liquid formed to be in contact with the first layer; and a third layer which includes a gelled hydrophobic ionic liquid formed in the opening so as to be in contact with the second layer. It is noted that, although as to be described in detail later, "hydrophobic ionic liquid" mainly means hydrophobic salt having a melting point of 100° C. or lower and a solubility to water in a degree of several mM ($mmol/dm^3$) or less, which includes a combination of organic or inorganic cation and organic or inorganic anion. Here, an ionic liquid is also called an ambient temperature molten salt or a room temperature molten salt and the like. Further, "reference electrode" is synonymous with a reference pole, a checking electrode, a reference electrode and a comparison electrode. Further, in the present description, "solution" and "liquid" are concepts including not only usual liquid but also a state capable of maintaining a state and shape of being gelled and flowing, unless it is not especially limited.

With this configuration, even if ions of the hydrophobic ionic liquid flow out of the third layer contacting the sample liquid into the sample liquid, ions are supplemented from the hydrophobic ionic liquid of the second layer so that the second layer functions as a buffer, and therefore the gel of the hydrophobic ionic liquid of the third layer can be prevented from being emaciated. Therefore, it is not necessary to form the gel of the hydrophobic ionic liquid of the third layer to be thick, and it can be formed to have a thickness in a degree capable of easily manufacturing while maintaining the prescribed hardness.

In addition, since the third layer is formed in the opening of the housing, the gelled hydrophobic ionic liquid can fill the opening so that only the minimum necessary quantity thereof for maintaining a seal function is sufficient to be used without necessity of making the thickness large.

Further, since the hydrophobic ionic liquid of the second layer is in a state of being covered with a lid by the third layer in the housing, a liquid or gelled hydrophobic ionic liquid having small hardness can be used without the necessity of maintaining the shape firmly with a single body of the second layer. That is, the second layer can include a liquid which is easily manufactured or a gelled hydrophobic ionic liquid having small hardness so that it is easy to sufficiently fill up a quantity necessary for supplementing the ions to the third layer.

In addition, since the first layer includes a water soluble electrolytic solution and the second layer includes a hydrophobic ionic liquid, the first and second layers are not melted together, and can be naturally separated from each other even if these layers are mixed.

For example, in such a case where the reference electrode is laterally laid, in order to prevent the water soluble electrolytic solution of the first layer and the hydrophobic ionic liquid of the second layer from being mixed together, the water soluble electrolytic solution of the first layer preferably may be gelled.

As a specific embodiment for allowing the reference electrode to be maintained in a state of being immediately usable all the time while the first and second layers are kept from mixture, the viscosity of the water soluble electrolytic solution of the first layer preferably may be equal to or larger than 100 mPa·s in a degree of not being emulsion.

In order to reduce the quantity of the hydrophobic ionic liquid firmly gelled for use in the reference electrode as much as possible so as to facilitate manufacture, the hydrophobic ionic liquid of the second layer preferably may be a non-gelled liquid.

In order to make it easier to prevent the first and second layers from being mixed together, the hydrophobic ionic liquid of the second layer preferably may be a gelled liquid. Further, in consideration of the manufacturing ease, the hardness or viscosity of the hydrophobic ionic liquid of the second layer preferably may be smaller than the hardness or viscosity of the hydrophobic ionic liquid of the third layer.

As a specific aspect for appropriately preventing the mixture of the first and second layers, the viscosity of the hydrophobic ionic liquid of the second layer preferably may be equal to or larger than 100 mPa·s and equal to or smaller than 1000 mPa·s.

Even if the first and second layers are mixed together, in order to naturally separate the first and second layers in this order, the specific gravity of the water soluble electrolytic solution of the first layer preferably may be smaller than the specific gravity of the hydrophobic ionic liquid of the second layer.

In order to reduce the quantity of the gelled hydrophobic ionic liquid of the third layer as small as possible so as to make it easier to fix the third layer to the opening, the opening preferably may be formed to have an outer side of the housing smaller than an inner side thereof.

In order to prevent the third layer from being disengaged from the opening due to weights of the first and second layers, etc., the viscosity of the hydrophobic ionic liquid of the third layer preferably may be equal to or larger than 1000 mPa·s.

In addition, a reference electrode of another aspect of the present invention is comprising an internal electrode and a housing that houses a filler for electrically connecting the internal electrode and a sample liquid, wherein the filler forms layers between the internal electrode and an opening formed in the housing for contacting the sample liquid and the filler, wherein the filler includes: a first layer which includes a water soluble electrolytic solution formed to be in contact with the internal electrode; a second layer which includes a hydrophobic ionic liquid formed to be in contact with the first layer; and a third layer which includes a porous material formed in the opening so as to be in contact with the second layer. It is noted that, although as to be described in detail later, "hydrophobic ionic liquid" mainly means hydrophobic salt having a melting point equal to or lower than 100° C. and a solubility to water in a degree of several mM (mmol/dm$^3$) or less, which includes a combination of organic or inorganic cation and organic or inorganic anion. Here, an ionic liquid is also called an ionic liquid or normally-dissolved salt and the like. Further, "reference electrode" is synonymous with a reference pole, a checking electrode, a reference electrode and a comparison electrode. Further, in the present description, "solution" and "liquid" are concepts including not only usual liquid but also a state capable of maintaining a state and shape of being gelled and flowing, unless it is not especially limited.

With this configuration, since the porous material of the third layer is in contact with the sample liquid while the hydrophobic ionic liquid of the second layer is not in direct contact with the sample liquid, the ions of the hydrophobic ionic liquid can be suppressed from flowing out into the sample liquid. Also, since the second layer is in a state of being covered with a lid by the third layer, it is not necessary to gel the hydrophobic ionic liquid of the second layer for maintaining the shape. Therefore, since it is also possible not to use the gelled hydrophobic ion, it is possible to eliminate the very problem that the seal function is deteriorated due to the gel being emaciated so that the product life cycle becomes short.

In addition, since the first layer includes a water soluble electrolytic solution and the second layer includes a hydrophobic ionic liquid, the first and second layers are not melted together, and can be naturally separated from each other even if these layers are mixed.

For example, in such a case where the reference electrode is laterally laid, in order to prevent the water soluble electrolytic solution of the first layer and the hydrophobic ionic liquid of the second layer from being mixed together, the water soluble electrolytic solution of the first layer preferably may be gelled.

As a specific embodiment for allowing the reference electrode to be maintained in a state of being immediately usable all the time while the first and second layers are kept from mixture, the viscosity of the water soluble electrolytic solution of the first layer preferably may be in a degree of suppressing emulsion, for example, 20 mPa·s, more preferably equal to or larger than 100 mPa·s.

In order to facilitate the manufacturing, the hydrophobic ionic liquid of the second layer preferably may be a non-gelled liquid.

In order to make it easier to prevent the first and second layers from being mixed together, the hydrophobic ionic liquid of the second layer preferably may be a gelled one. Further, in consideration of the manufacturing ease, the hardness or viscosity of the hydrophobic ionic liquid of the second layer preferably may be smaller than the hardness or viscosity of the hydrophobic ionic liquid of the third layer.

As a specific aspect for appropriately preventing the mixture of the first and second layers and capable of facilitating the manufacturing, the viscosity of the hydrophobic ionic liquid of the second layer preferably may be equal to or larger than 300 mPa·s and equal to or smaller than 1000 mPa·s.

Even if the first and second layers are mixed together, in order to naturally separate the first and second layers in this order, the specific gravity of the water soluble electrolytic solution of the first layer preferably may be smaller than the specific gravity of the hydrophobic ionic liquid of the second layer.

In order to prevent the hydrophobic ionic liquid of the second layer itself from passing through the porous material of the third layer so as to directly flow out into the sample liquid, the porous material of the third layer preferably may be hydrophilic. With this configuration, since the second layer includes the hydrophobic ionic liquid, it is to be rejected on a surface of the hydrophilic porous material and can be prevented from passing through the third layer.

As another aspect for preventing the outflow of the hydrophobic ionic liquid of the second layer itself, a diameter of each hole of the porous material of the third layer preferably may be in a degree that the hydrophobic ionic liquid of the second layer cannot enter.

As a preferable embodiment to prevent the hydrophobic ionic liquid from flowing out, the diameter of each hole of the porous material of the third layer preferably may be in a range of 100 nm to 100 μm.

As a specific embodiment of the porous material, the porous material of the third layer may be polycarbonate.

Advantageous Effects of Invention

Thus, according to the reference electrode of the present invention, since the second layer acts as a buffer so that ions are appropriately supplemented even if the ions of the hydrophobic ionic liquid flow out from the third layer contacting the sample liquid, the gel of the third layer can be prevented from being emaciated. Accordingly, there is no problem even if the third layer is thin, and since it is not necessary to make a gel of a hard and thick hydrophobic ionic liquid, it can be made very easy to manufacture. Moreover, since the seal function by the hydrophobic ionic liquid is continued to be maintained, the product life cycle can be made longer than the conventional life cycle and a state capable of preventing fluctuations can be kept for a long period.

Further, according to the reference electrode of another aspect of the present invention, since it is configured that the hydrophobic ionic liquid of the second layer is not in direct contact with the sample liquid by the porous material of the third layer, the ions of the hydrophobic ionic liquid can be prevented from flowing out into the sample liquid. Also, since the second layer is in a state of being covered with a lid by the third layer, it is not necessary to make a gelled layer of large hardness for maintaining the shape. Therefore, a material that is easy to manufacture, such as a liquid or gel of small hardness, can be used as the hydrophobic ionic liquid of the second layer. Accordingly, it is also possible not to use the gelled hydrophobic ionic liquid and it is possible to eliminate the very problem that the gel of the hydrophobic ionic liquid is emaciated so that the product life cycle becomes short.

REFERENCE CHARACTERS LIST

Figure 1:
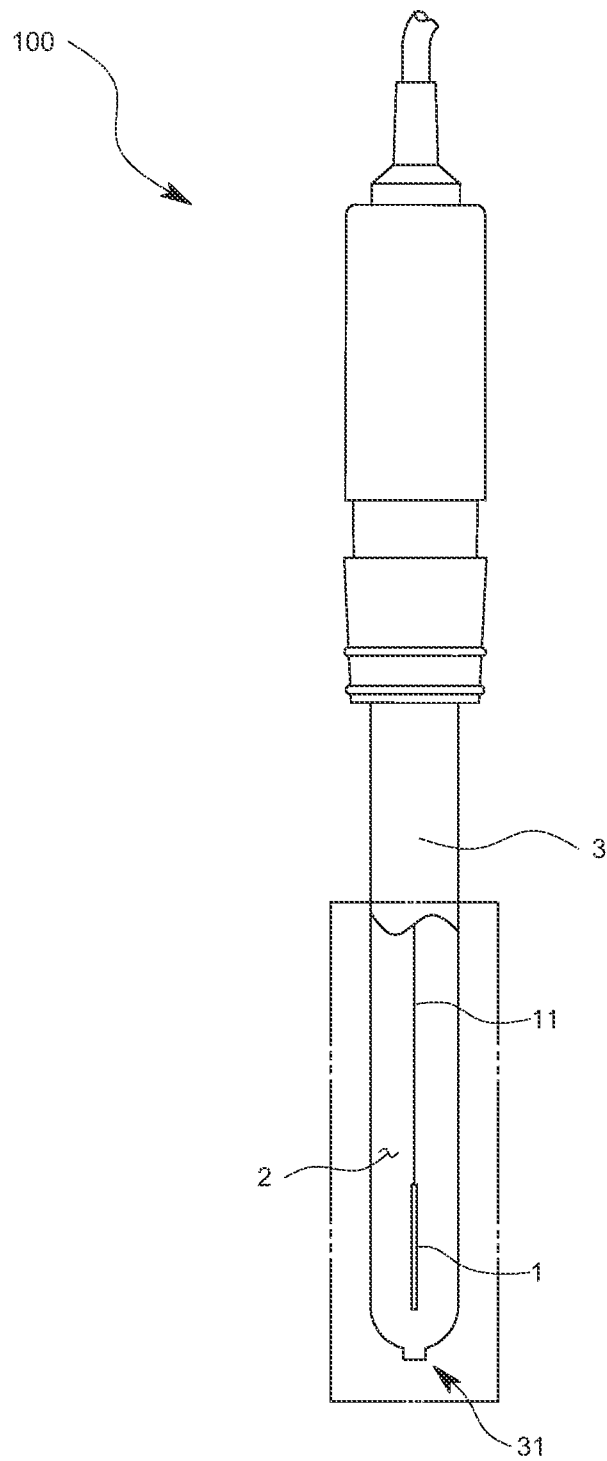
FIG. 1 is a schematic diagram showing a reference electrode according to a first embodiment of the present invention.

100 . . . Reference electrode
1 . . . Internal electrode
2 . . . Filler
21 . . . First layer
22 . . . Second layer
23 . . . Third layer
3 . . . Support tube (housing)
4 . . . Sample liquid

DESCRIPTION OF EMBODIMENTS

The following describes one embodiment of the present invention with reference to the drawings.

Figure 2:
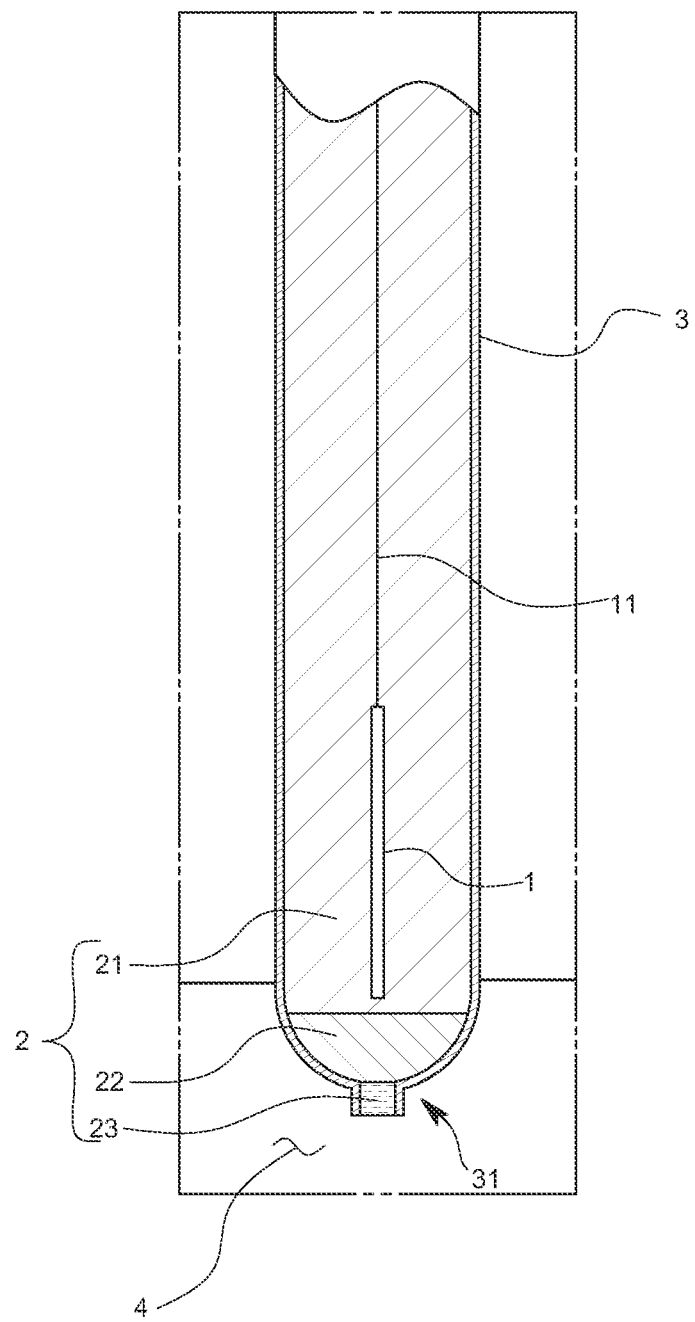
FIG. 2 is a schematic sectional view showing an internal structure in a tip end of a support tube in the same embodiment.

A reference electrode 100 according to the first embodiment is provided with a generally cylindrical shaped glass support tube 3 (corresponding to a housing of the present invention) as shown in a schematic outline diagram of FIG. 1 and in a state of being immersed in a sample liquid as shown in an enlarged view of FIG. 2. Inside this support tube 3, an internal electrode 1 is accommodated and it is filled with a filler 2 which electrically connects the internal electrode 1 and the sample liquid 4. A lead wire 11 is connected to the internal electrode 1 and the lead wire 11 is configured to be extended from a proximal end portion of this support tube 3 to the outside so as to be connected to measurement equipment (not shown).

A tip end of the support tube 3 is opened to form an opening 31 so that the sample liquid 4 and the filler 2 can be contacted and a tip center part thereof is projected so that an outer diameter is made smaller compared to that of the proximal end side.

The internal electrode 1 is, for example, an Ag/AgCl electrode and it is configured by coating internal silver with silver chloride. As the other aspects, also an $Hg/Hg_2Cl_2$ electrode and an $Hg/Hg_2SO_4$ electrode may be used.

The filler 2 is rendered to fill in a manner of forming a plurality of layers between the internal electrode 1 and the opening 31 positioned at the tip end of the support tube 3 as shown in FIG. 2. More specifically, the filler 2 is comprised of; a first layer 21 which includes a water soluble electrolytic solution and formed to be in contact with the internal electrode 1; a second layer 22 which includes a hydrophobic ionic liquid and formed to be in contact with the first layer 21; and a third layer 23 which includes a gelled hydrophobic ionic liquid formed to be in contact with the second layer 22 and formed in the opening 31.

The water soluble electrolytic solution of the first layer 21 is, for example, a KCl solution. It is noted that, in the case where the internal electrode 1 includes Ag/AgCl, a solution containing Cl− can be used as the water soluble electrolytic solution unless it enters into the hydrophobic ionic liquid of the second layer 22 as to be described later. In addition, since generation of a liquid junction potential can be suppressed by the hydrophobic ionic liquid of the second layer to be described later functioning as a salt bridge, for example, a NaCl solution etc. may be used. In addition, an electrolytic solution etc. including Cl− and cation same as the positive ion of the hydrophobic ionic liquid to be described later may be used. This is because there is not especially any problem even if the cation same as the ion of the hydrophobic ionic liquid enters from the electrolytic solution.

This KCl solution is gelled and covers the internal electrode 1 all the time and is provided at least around the internal electrode 1 with its viscosity sufficient to seal the inside of the support tube 3 in the periphery thereof. Herein, as a method of gelling the water soluble electrolytic solution, it is not especially limited and, for example, there can be listed a method of using polymer such as a vinylidene fluoride-hexafluoropropylene copolymer, polymethylmethacrylate, polyacrylonitrile, poly butyl acrylate, and other synthetic rubbers. The viscosity of gel is adjusted by adjusting the mixture ratio of a water-soluble electrolytic solution and polymer. Further, the viscosity of the gel is adjusted by adjusting a mixture ratio of the water soluble electrolytic solution and the polymer. More specifically, the viscosity of the water soluble electrolytic solution of the first layer 21 is made equal to or larger than 100 mPa·s.

As the hydrophobic ionic liquid of the second layer 22, there can be listed a liquid in which a cation is at least one or more of the quaternary ammonium cation, the quaternary phosphonium cation, or the quaternary arsonium cation while an anion is at least one or more of $[R_1SO_2NSO_2R_2]^-$ (R1 and R2 are the perfluoroalkyl groups of the carbon numbers 1-5, respectively), borate ion containing fluoride and tetravalent boron, bis(2-ethylhexyl) sulfosuccinate, $AlCl_4^-$, $Al_3Cl_7^-$, $NO_3^-$, $BF_4^-$, $PF_6^-$, $CH_3COO^-$, $CF_3COO^-$, $CF_3SO_3^-$, $(CF_3SO_2)_2N^-$, $(CF_3SO_2)_3C^-$, $AsF_6^-$, $SbF_6^-$, $F(HF)_n^-$, $CF_3CF_2CF_2SO_3^-$, $(CF_3CF_2SO_2)_2N^-$ or $CF_3CF_2CF_2COO^-$, and among these hydrophobic ionic liquids, an appropriate one is selected and used in accordance with the usage.

This hydrophobic ionic liquid of the second layer 22 is a non-gelled liquid and it is allowed to be easily manufactured even if the thickness of the second layer 22 is large. In addition, the specific gravity of the electrolytic solution of the first layer 21 is made smaller than the specific gravity of the hydrophobic ionic liquid of the second layer 22.

The third layer 23 is a gelled film of the hydrophobic ionic liquid provided in a manner of closing the opening 31 and has the same composition as that of the hydrophobic ionic liquid of the second layer 22. The third layer 23 together with the second layer 22 functions as a salt bridge and is rendered to exhibit a seal function so that the sample liquid 4 may not directly contact the inside of the support tube 3 by provision of the third layer 23. A method of gelling this hydrophobic ionic liquid is similar to a method of gelling the water soluble electrolytic solution mentioned before, and the viscosity thereof is set such that the third layer 23 is not disengaged even if weights of the first and second layers 21 and 22 are applied. More specifically, the viscosity of the hydrophobic ionic liquid of the third layer 23 is made equal to or larger than 1000 mPa·s.

According to the reference electrode 100 configured like this, even if the ions composing the gel of the hydrophobic ionic liquid itself flow out caused by contact between the gel of the hydrophobic ionic liquid of the third layer 23 and the sample liquid 4, the hydrophobic ionic liquid of the second layer 22 acts as a buffer so that ions are supplemented. Therefore, since reduction of the gel due to outflow of the composition ions can be prevented, the life cycle can be increased without making a gel hydrophobic ionic liquid having a large thickness and hardness which is difficult to be manufactured. Accordingly, it is not necessary to form a thick gel of the hydrophobic ionic liquid of the third layer 23 so that the gel can be previously formed with a thickness in a degree of being able to easily manufactured while maintaining predetermined hardness.

Moreover, since only the opening 31 opened with a small diameter in a part of the tip end of the support tube 3 is to be closed, the gel film of the hydrophobic ionic liquid can be made thin in a degree of being able to be easily manufactured.

Furthermore, since the third layer 23 is in a gelled state so as to close the opening 31 and is in a state of being covered with a lid, it is not necessary that the second layer 22 itself maintains the shape and the hydrophobic ionic liquid of the second layer 22 can be used as a liquid. That is, since it is not necessary to be hardened, it can be easily manufactured at a low cost even if the thickness of the second layer 22 is made large, there can be obtained a sufficient quantity for functioning as a buffer with respect to the third layer 23 for a long period.

In addition, since the first layer 21 includes a water soluble electrolytic solution and the second layer 22 includes a hydrophobic ionic liquid, the first layer 21 and second layer 22 are not melted together and can be naturally separated from each other even if these layers are mixed, and yet since the specific gravity of the first layer 21 is smaller than that of the second layer 22, the arrangement order of the layers can be returned back to the original order merely by vertically setting up the reference electrode 100.

Moreover, since the water soluble electrolytic solution of the first layer 21 is gelled so that there exists no gap within the support tube 3, the first layer 21 and the second layer 22 can be prevented from mixing together even in the case where the reference electrode 100 is laterally laid.

The other embodiments of the first embodiment will be described below.

Although the hydrophobic ionic liquid of the second layer is in a non-gelled liquid state in the first embodiment, the liquid may be gelled. In this case, it is preferable to be in a softer gelled state than the hardness of the gel of the hydrophobic ionic liquid of the third layer so as to facilitate manufacture. The specific viscosity of the hydrophobic ionic liquid of the second layer preferably may be in a range equal to or larger than 100 mPa·s and equal to or smaller than 1000 mPa·s. By gelling the second layer in this range, the manufacturing can be facilitated, and the first layer and the second layer can be also prevented from mixing together.

Moreover, although the water soluble electrolytic solution of the first embodiment is gelled in the first embodiment, non-gelled liquid may be used. Herein, regarding the non-gelled liquid state where the water soluble electrolytic solution or ionic liquid is not gelled, there can be exemplified, for example, a state that each liquid and polymer for gelling are not mixed and a state that there occurs substantially no change in viscosity etc. even if only a very slight quantity of polymer is mixed. Further, regarding the softer gelled state, there can be exemplified a state that, for example, the water soluble electrolytic solution or ionic liquid cannot retain a shape in a single body while having a viscosity higher than that in a non-gelled liquid state.

Figure 3:
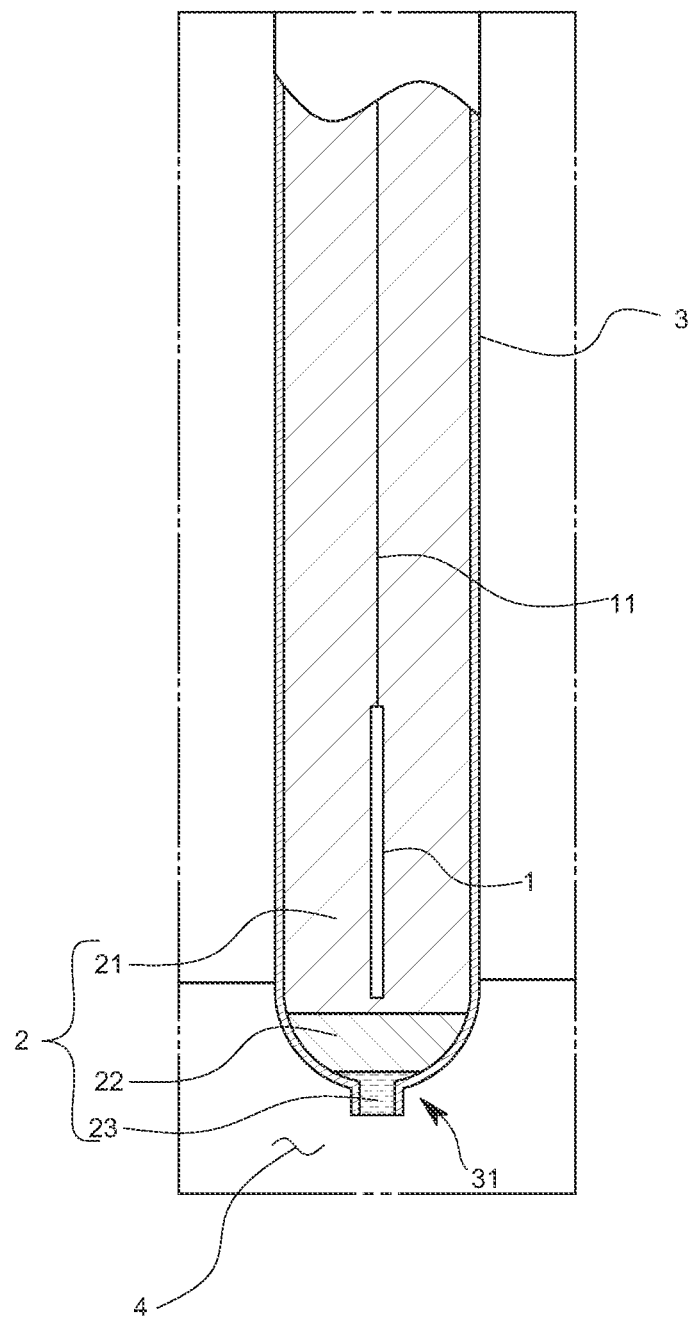
FIG. 3 is a schematic sectional view showing an internal structure in a tip end of a support tube in another embodiment of the first embodiment.

Although the third layer is provided in such a manner of closing only the projected portion in the tip end of the support tube in the first embodiment, the thickness of the layer may further extend to the inner side within an easy manufacturing range. As shown in FIG. 3, if the third layer 23 is formed to be a gel having a thin plate-like central portion slightly projected, the third layer 23 is formed to have a hook place to be caught by the support tube so that the third layer 23 can be made harder to be disengaged with respect to the opening 31. Further, by previously providing a porous material in the opening 31 while the holes thereof are dampened with a gelled hydrophobic ionic liquid, the third layer 23 may be made to be easily held.

Figure 4:
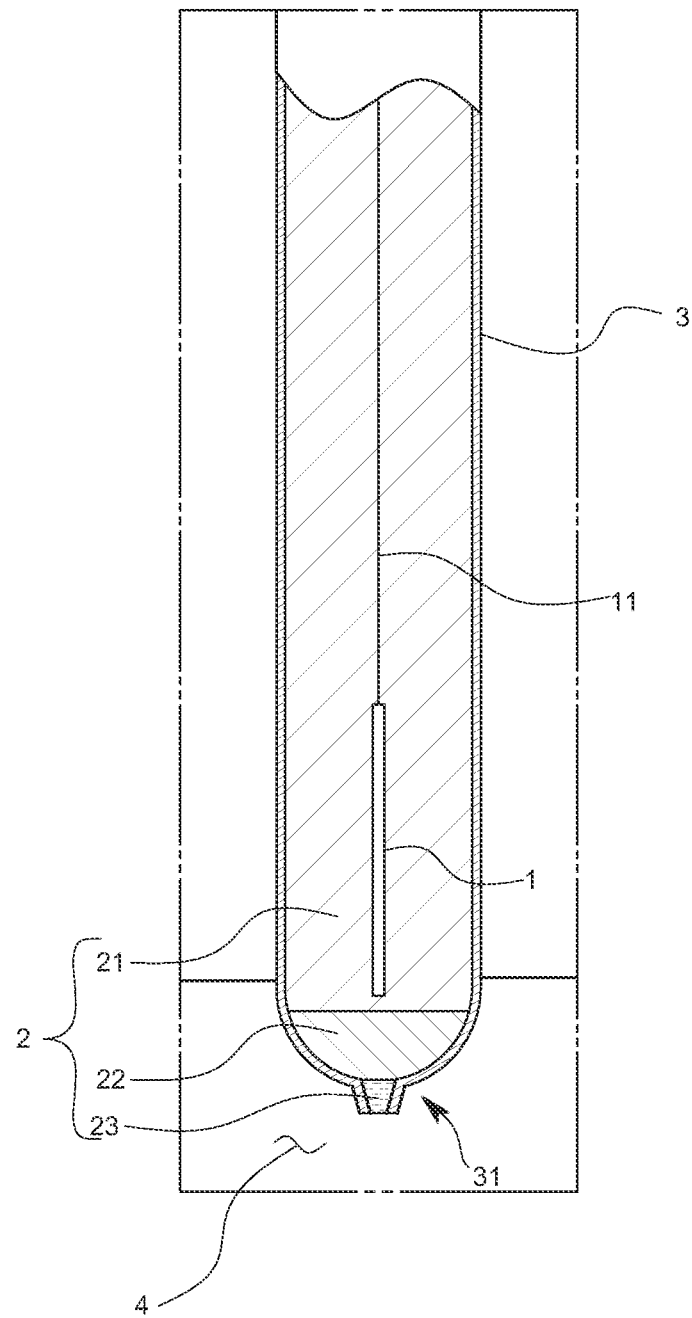
FIG. 4 is a schematic sectional view showing an internal structure in a tip end of a support tube in further another embodiment of the first embodiment.

In addition, although the opening 31 is formed to be a straight hole in the first embodiment, for example, as shown in FIG. 4, the opening 31 may be formed to have a tapered shape so that the opening diameter inside the support tube 3 may be made larger than the opening diameter of the tip end side. Also, with this configuration, the gelled hydrophobic ionic liquid of the third layer can be easily prevented from disengagement.

In addition, the thicknesses of the first and second layers can also be appropriately changed, for example, the internal electrode may be in contact with the first and second layers. In this case, it may be preferable to keep a reference voltage from varying by using compensation means such as temperature compensation. Also, it may be used for such as ion concentration measurement and pH measurement by combining the reference electrode of the present invention and various electrodes for measurement.

The following describes a second embodiment of the present invention with reference to drawings.

Figure 5:
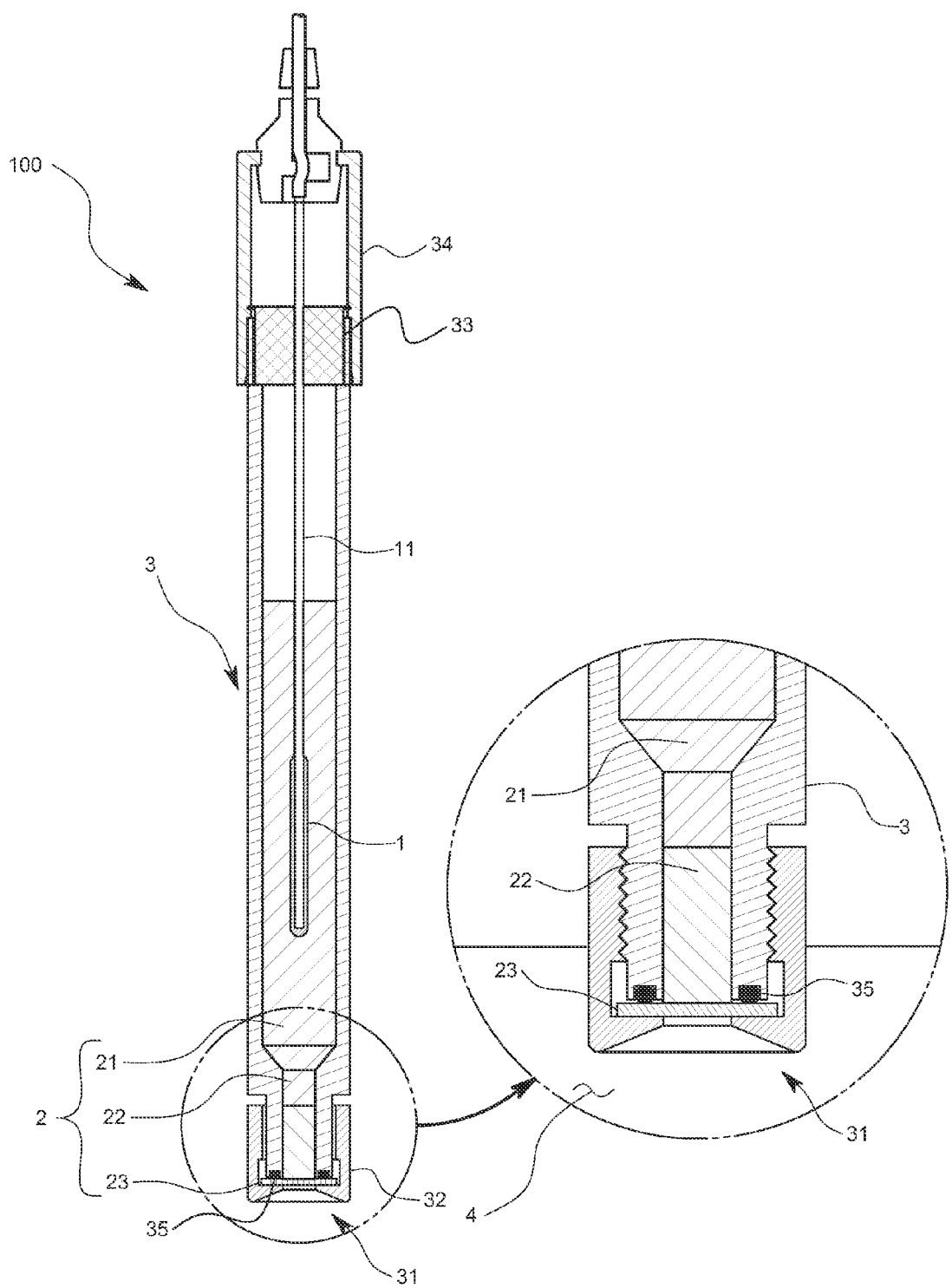
FIG. 5 is a schematic diagram showing a reference electrode according to a second embodiment of the present invention.

A reference electrode 100 according to the second embodiment includes a cylindrical shaped support tube 3 (corresponding to a housing of the present invention) and an opening 31 provided at a tip end portion of the support tube 3 as shown in FIG. 5, and inside of the support tube 3 is filled with a filler 2 which electrically connects the internal electrode 1 and the sample liquid 4. The filler 2 is layered, and especially a film of a porous material of a third layer 23 provided in the opening 31 is fixed to the support tube 3 by a film fixing part 32.

The support tube 3 is adapted to accommodate the internal electrode 1 and the filler 2, and as the materials thereof, resins such as PP, PE, acrylic, PTFE ((poly tetra fluoro ethylene resin), PVDF (poly vinylidene difluoride resin) and PEEK (polyether ether ketone resin), glass, metal, ceramic, etc., can be considered. The present embodiment is molded using PVDF. At a proximal end of the support tube 3, there are provided a seal packing 33 which liquid-densely contacts the proximal end and a cap 34 covering the seal packing 33 so that the filler 2 does not leak out of the support tube 3.

Further, the tip end portion of the support tube 3 is reduced in size of the outer diameter, and a male thread part 32a is provided on an outer peripheral surface of the tip end portion thereof so that the male thread part 32a and a film fixing part 32 having a female thread part formed on a substantially cylindrical shaped inner peripheral surface thereof are screwed. Further, on a tip end surface of the tip end portion, there is provided an accommodation slot for accommodating an O ring 35 concentrically with a center axis of the support tube 3. And a film made of a porous material which is the third layer 23 is provided in a manner of covering over the tip end surface.

The internal electrode 1 is, for example, an Ag/AgCl electrode and it is configured by coating internal silver with silver chloride. As the other aspects, also an Hg/Hg$_2$Cl$_2$ electrode and an Hg/Hg$_2$SO$_4$ electrode may be used.

The filler 2 is rendered to fill in a manner of forming a plurality of layers between the internal electrode 1 and the opening 31 positioned at the tip end of the support tube 3 as shown in FIG. 5. More specifically, the filler 2 is comprised of; a first layer 21 which includes a water soluble electrolytic solution and formed to be in contact with the internal electrode 1; a second layer 22 which includes a hydrophobic ionic liquid and formed to be in contact with the first layer 21; and a third layer 23 which includes a gelled hydrophobic ionic liquid formed to be in contact with the second layer 22 and formed in the opening 31.

The water soluble electrolytic solution of the first layer 21 is, for example, a KCl solution. It is noted that, in the case where the internal electrode 1 includes Ag/AgCl, a solution containing Cl− can be used as the water soluble electrolytic solution unless it enters into the hydrophobic ionic liquid of the second layer 22 as to be described later. In addition, since generation of a liquid junction potential can be suppressed by the hydrophobic ionic liquid of the second layer to be described later functioning as a salt bridge, for example, a NaCl solution etc. may be used. In addition, an electrolytic solution etc. including Cl− and cation same as the positive ion of the hydrophobic ionic liquid to be described later may be used. This is because there is especially no problem even if the cation same as the ion of the hydrophobic ionic liquid enters from the electrolytic solution.

This KCl solution is gelled and covers the internal electrode 1 all the time and is provided at least around the internal electrode 1 with its viscosity sufficient to seal the inside of the support tube 3 in the periphery thereof. Herein, as a method of gelling the water soluble electrolytic solution, it is not especially limited and, for example, there can be listed a method of using polymer such as a vinylidene fluoride-hexafluoropropylene copolymer, polymethylmethacrylate, polyacrylonitrile, poly butyl acrylate, and other synthetic rubbers. The viscosity of gel is adjusted by adjusting the mixture ratio of a water soluble electrolytic solution and polymer. More specifically, the viscosity of the water soluble electrolytic solution of the first layer 21 is set to be in a degree of suppressing emulsion, for example, set to equal to or larger than 20 mPa·s, more preferably equal to or larger than 100 mPa·s.

As the hydrophobic ionic liquid of the second layer 22, there can be listed a liquid in which a cation is at least one or more of the quaternary ammonium cation, the quaternary phosphonium cation, or the quaternary arsonium cation while an anion is at least one or more of $[R_1SO_2NSO_2R_2]^-$ (R1 and R2 are the perfluoroalkyl groups of the carbon numbers 1-5, respectively), borate ion containing fluoride and tetravalent boron, bis(2-ethylhexyl) sulfosuccinate, $AlC_4^-$, $Al_3Cl_7^-$, $NO_3^-$, $BF_4^-$, $PF_6^-$, $CH_3COO^-$, $CF_3COO^-$, $CF_3SO_3^-$, $(CF_3SO_2)_2N^-$, $(CF_3SO_2)_3C^-$, $AsF_6^-$, $SbF_6^-$, $F(HF)_n^-$, $CF_3CF_2CF_2CF_2SO_3^-$, $(CF_3CF_2SO_2)_2N^-$ or $CF_3CF_2CF_2COO^-$, and among these hydrophobic ionic liquids, an appropriate one is selected and used in accordance with the usage so that the liquid exhibits a function as a salt bridge between the water soluble electrolytic solution of the first layer 21 and the sample liquid.

This hydrophobic ionic liquid of the second layer 22 is a non-gelled liquid and it is allowed to be easily manufactured even if the thickness of the second layer 22 is large. In addition, the specific gravity of the electrolytic solution of the first layer 21 is made smaller than the specific gravity of the hydrophobic ionic liquid of the second layer 22.

The third layer 23 is provided in a manner so as to close the opening 31 and is used as a porous membrane by polycarbonate. Although this porous membrane is hydrophilic and contains moisture in the sample liquid 4, the hydrophobic ionic liquid is rendered to be crawled on the surface. Further, a diameter of a hole of the porous membrane is in a degree of 100 nm to 100 μm and it is configured such that the hydrophobic ionic liquid of the second layer 22 cannot enter the inside of the porous membrane by configuring a material property such as surface tension. The viscosity of the hydrophobic ionic liquid preferably may be set higher in the case where the diameter of the hole is larger so that the surface tension, etc., may function well.

According to the reference electrode 100 configured like this, since the porous membrane of the third layer 23 contacts the sample liquid 4 while the hydrophobic ionic liquid of the second layer 22 does not directly contact the sample liquid, the ions composing the hydrophobic ionic liquid can be prevented from flowing out into the sample liquid 4. Moreover, since the second layer 22 is in a state of being closed with a lid by the third layer 23 in the support tube 3, it is not necessary to gel the hydrophobic ionic liquid for maintaining a shape. Therefore, the gelled hydrophobic ionic liquid can be rendered to be unused for the reference electrode 100, and it is possible to eliminate the very problem that the sealing function is deteriorated due to the gel being emaciated so that the life cycle is shortened.

In addition, since the first layer 21 includes a water soluble electrolytic solution and the second layer 22 includes a hydrophobic ionic liquid, the first layer 21 and second layer 22 are not melted together and can be naturally separated from each other even if these layers are mixed, and yet since the specific gravity of the first layer 21 is smaller than that of the second layer 22, the arrangement order of the layers can be returned back to the original order merely by vertically setting up the reference electrode 100.

Moreover, since the water soluble electrolytic solution of the first layer 21 is gelled so that there exists no gap within the support tube 3, the first layer 21 and the second layer 22 can be prevented from mixing together even in the case where the reference electrode 100 is laterally laid.

The other embodiments of the second embodiment will be described below. Although the porous membrane of the third layer is fixed by pinching between a main body of the support tube and the film fixing part 33 in the second embodiment, it may be provided in the opening 31 by the other method. For example, the porous membrane may be thermally fusion-bonded in a manner of covering the tip end of the film fixing part 33. Also, the porous membrane may be thermally fusion-bonded to the tip end of the main body of the support tube 3.

Although the hydrophobic ionic liquid of the second layer is in a non-gelled liquid state in the second embodiment, the liquid may be gelled. In this case, it is preferable to be in a soft gelled state so as to facilitate manufacture. A specific viscosity of the hydrophobic ionic liquid of the second layer preferably may be in a range equal to or larger than 300 mPa·s and equal to or smaller than 1000 mPa·s. By gelling the second layer in this range, manufacture can be facilitated, and the first layer and the second layer can be also prevented from mixing together. In addition, the hydrophobic ionic liquid may be also gelled by the same method as the method of gelling the water soluble electrolytic solution.

Moreover, although the water soluble electrolytic solution of the first embodiment is gelled in the second embodiment, non-gelled liquid may be used.

Figure 6:
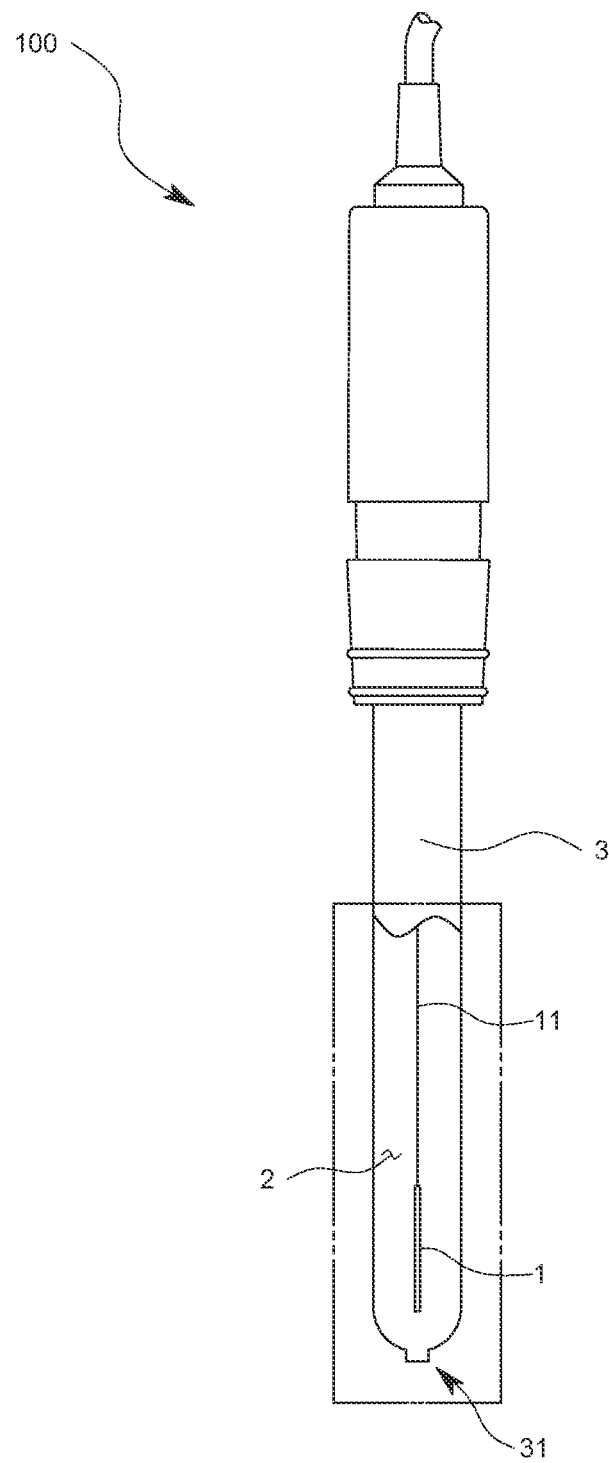
FIG. 6 is a schematic diagram showing a reference electrode according to a third embodiment of the present invention.
Figure 7:
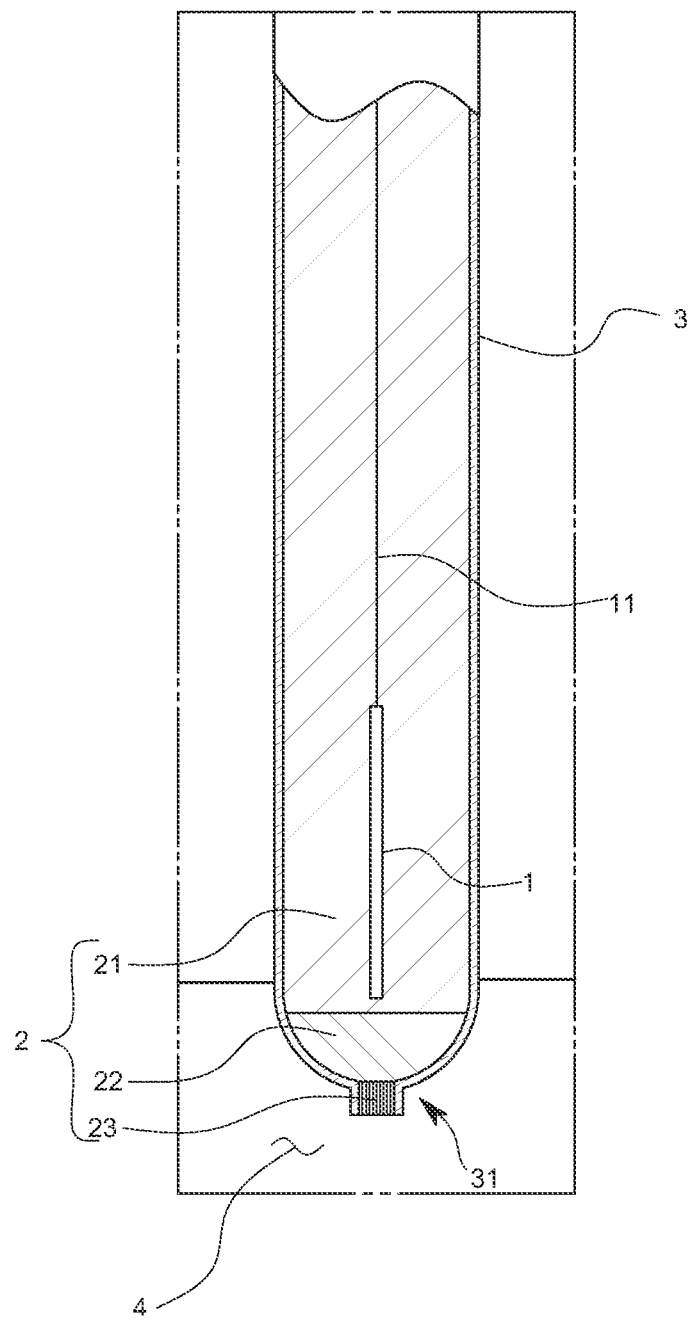
FIG. 7 is a schematic sectional view showing an internal structure in a tip end of a support tube in the third embodiment.

The reference electrode 100 may be a multi pinhole typed electrode different from the embodiment mentioned above. More specifically, the reference electrode 100 of the third embodiment is provided with a generally cylindrical shaped glass support tube 3 (corresponding to a housing of the present invention) as shown in a schematic outline diagram of FIG. 6 and in a state of being immersed in a sample liquid 4 as shown in an enlarged view of FIG. 7. Inside this support tube 3, an internal electrode 1 is accommodated and it is filled with a filler 2 which electrically connects the internal electrode 1 and the sample liquid 4. A lead wire 11 is connected to the internal electrode 1 and the lead wire 11 is configured to be extended from a proximal end portion of this support tube 3 to the outside so as to be connected to measurement equipment (not shown).

A tip end of the support tube 3 is opened to form an opening 31 so that the sample liquid 4 and the filler 2 can be contacted and a tip center part thereof is projected so that an outer diameter is made smaller compared to that of the proximal end side.

Figure 8:
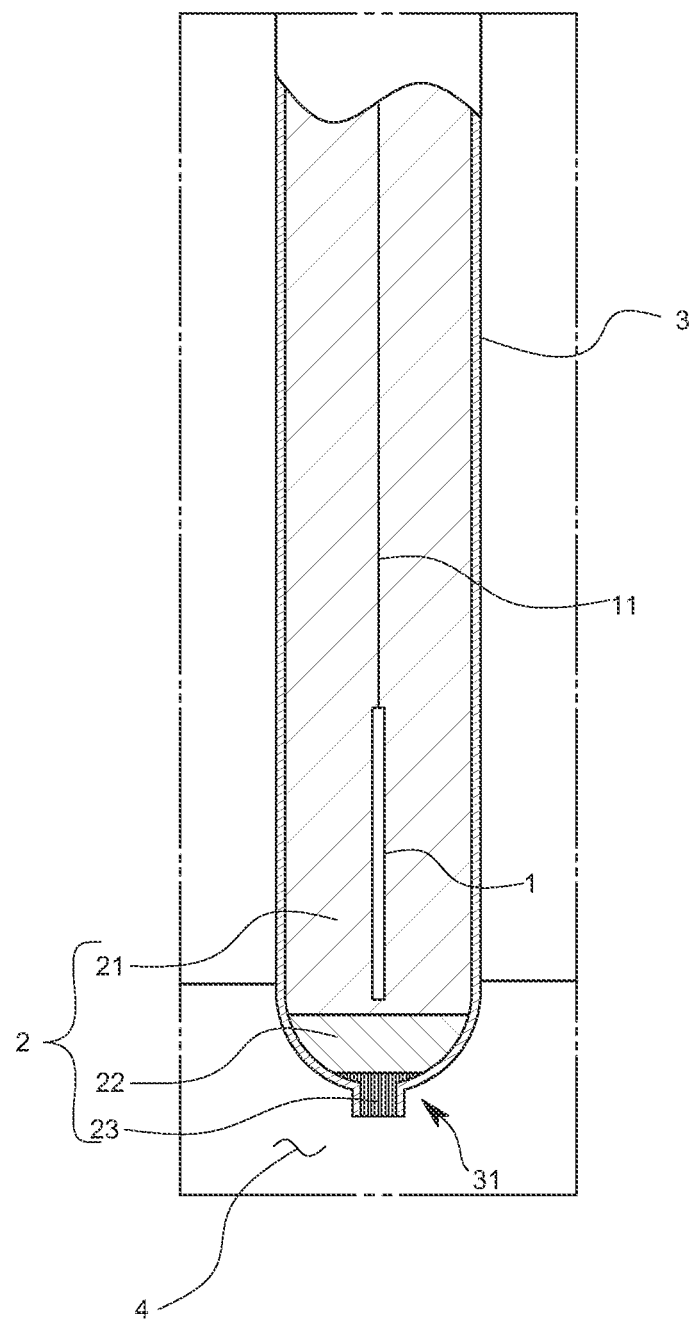
FIG. 8 is a schematic sectional view showing an internal structure in a tip end of a support tube in a modified embodiment of the third embodiment.

Although the third layer is provided in such a manner of closing only the projected portion in the tip end of the support tube in the third embodiment, the thickness of the layer may further extend to the inner side. As shown in FIG. 8, if the third layer 23 is formed to be a porous membrane having a thin plate-like central portion slightly projected, the third layer 23 is formed to have a hook portion to be caught by the support tube 3 so that the third layer 23 can be easily fixed.

Figure 9:
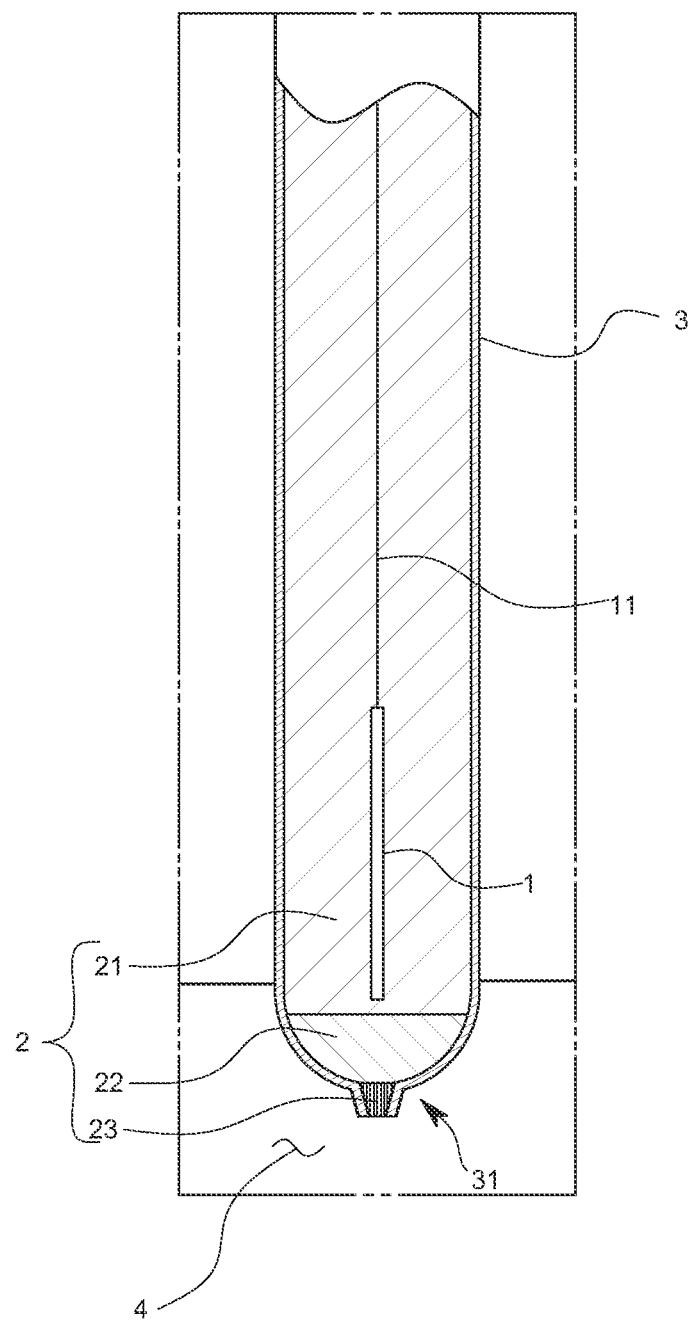
FIG. 9 is a schematic sectional view showing an internal structure in a tip end of a support tube in a modified embodiment of the third embodiment.

In addition, although the opening 31 is formed to be a straight hole in the third embodiment, for example, as shown in FIG. 9, the opening 31 may be formed to have a tapered shape so that the opening diameter inside the support tube 3 may be made larger than the opening diameter of the tip end side. With this configuration, the porous membrane of the third layer can be easily prevented from being disengaged from the opening 31.

In addition, the thicknesses of the first and second layers can also be appropriately changed, for example, the internal electrode may be in contact with the first and second layers. In this case, it may be preferable to keep a reference voltage from varying by using compensation means such as temperature compensation. Also, it may be used for such as ion concentration measurement and pH measurement by combining the reference electrode of the present invention and various electrodes for measurement.

Although the porous material of the third layer is formed in a film state in each of the embodiments, it may be formed in a shape other than a film. In addition, it may be possible to use materials other than polycarbonate, and the third layer may be a porous sheet like film, etc., using glass of glass fiber, ceramic and thermoplastic resin as a raw material. As the thermoplastic resin, polypropylene, polyethylene, polyester, nylon, PET, etc., may be exemplified other than polycarbonate. Moreover, for example, the holes of the porous material of the third layer may be adjusted in accordance with the viscosity of the hydrophobic ionic liquid of the second layer. Specifically, it may be also possible that, multiple pinholes are formed in a member of the third layer so as to be a porous material, and by adjusting the hole diameters and number thereof, the internal electrode and the sample liquid are appropriately electrically connected so that the hydrophobic ionic liquid itself is prevented from flowing out to the sample liquid through the holes.

In addition, various modifications and combination of the embodiments may be made unless it is contrary to the spirit of the present invention.

INDUSTRIAL APPLICABILITY

According to the reference electrode of the present invention, it is not necessary to make a gel of a hard and thick hydrophobic ionic liquid, and it can be made very easy to manufacture, and the product life cycle can be made longer than the conventional life cycle and a state capable of preventing fluctuations can be kept for a long period.

The invention claimed is:

1. A reference electrode comprising an internal electrode and a housing that houses a filler for electrically connecting the internal electrode and a sample liquid, wherein
the filler forms layers between the internal electrode and an opening formed in the housing for contacting the sample liquid and the filler, wherein the filler comprises:
a first layer which includes a water soluble electrolytic solution formed to be in contact with the internal electrode;
a second layer which includes a hydrophobic ionic liquid formed to be in contact with the first layer; and a third layer which includes a gelled hydrophobic ionic liquid formed in the opening so as to be in contact with the second layer.

2. The reference electrode according to claim 1, wherein the water soluble electrolytic solution of the first layer is a gelled solution.

3. The reference electrode according to claim 1, wherein the hydrophobic ionic liquid of the second layer is a non-gelled liquid.

4. The reference electrode according to claim 1, wherein a specific gravity of the water soluble electrolytic solution of the first layer is lighter than that of the hydrophobic ionic liquid of the second layer.

5. The reference electrode according to claim 1, wherein a viscosity of the hydrophobic ionic liquid of the third layer is equal to or larger than 1000 mPa·s.

6. A reference electrode comprising an internal electrode and a housing that houses a filler for electrically connecting the internal electrode and a sample liquid, wherein the filler forms layers between the internal electrode and an opening formed in the housing for contacting the sample liquid and the filler, wherein the filler comprises:

a first layer which includes a water soluble electrolytic solution formed to be in contact with the internal electrode;

a second layer which includes a hydrophobic ionic liquid formed to be in contact with the first layer; and a third layer which includes a porous material formed in the opening so as to be in contact with the second layer.

7. The reference electrode according to claim 6, wherein the water soluble electrolytic solution of the first layer is a gelled solution.

8. The reference electrode according to claim 6, wherein the hydrophobic ionic liquid of the second layer is a gelled liquid.

9. The reference electrode according to claim 6, wherein a specific gravity of the water soluble electrolytic solution of the first layer is lighter than that of the hydrophobic ionic liquid of the second layer.

* * * * *